US010968429B2

(12) United States Patent
Matsumoto et al.

(10) Patent No.: US 10,968,429 B2
(45) Date of Patent: Apr. 6, 2021

(54) CHELATED IRON-CONTAINING CULTURE MEDIUM FOR NEURAL STEM CELLS

(71) Applicant: AJINOMOTO CO., INC., Tokyo (JP)

(72) Inventors: Takuya Matsumoto, Kawasaki (JP); Sho Senda, Kawasaki (JP); Tsuyoshi Kobayashi, Kawasaki (JP); Akihiro Arakawa, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 276 days.

(21) Appl. No.: 15/718,574

(22) Filed: Sep. 28, 2017

(65) Prior Publication Data

US 2018/0051250 A1  Feb. 22, 2018

Related U.S. Application Data

(63) Continuation of application No. PCT/JP2016/060552, filed on Mar. 30, 2016.

(30) Foreign Application Priority Data

Mar. 30, 2015 (JP) .............................. JP2015-069978

(51) Int. Cl.
*C12N 5/0797* (2010.01)
*C12N 5/10* (2006.01)
*A61L 27/00* (2006.01)
*A61K 35/30* (2015.01)

(52) U.S. Cl.
CPC ............ *C12N 5/0623* (2013.01); *A61K 35/30* (2013.01); *A61L 27/00* (2013.01); *C12N 5/10* (2013.01); *C12N 2500/24* (2013.01); *C12N 2500/46* (2013.01); *C12N 2501/115* (2013.01); *C12N 2506/03* (2013.01); *C12N 2506/45* (2013.01)

(58) Field of Classification Search
CPC ........... A61L 27/00; A61K 35/30; C12N 5/10; C12N 5/0623; C12N 2506/45; C12N 2500/46; C12N 2501/115; C12N 2506/03; C12N 2500/24
See application file for complete search history.

(56) References Cited

U.S. PATENT DOCUMENTS

| 2002/0076747 | A1 | 6/2002 | Price et al. |
| 2002/0197238 | A1 | 12/2002 | Weiss et al. |
| 2005/0095702 | A1 | 5/2005 | Alam et al. |
| 2006/0148074 | A1 | 7/2006 | Gorfien et al. |
| 2007/0031964 | A1 | 2/2007 | Osborne et al. |
| 2007/0059823 | A1 | 3/2007 | Verfaillie et al. |
| 2008/0227136 | A1 | 9/2008 | Pla et al. |
| 2009/0104695 | A1* | 4/2009 | Shushan et al. ............. 435/366 |
| 2011/0052548 | A1 | 3/2011 | Chin et al. |
| 2011/0182853 | A1 | 7/2011 | Weiss et al. |
| 2011/0182983 | A1 | 7/2011 | Juliusson |
| 2011/0229441 | A1 | 9/2011 | Benchoua et al. |
| 2012/0077213 | A1 | 3/2012 | Pla et al. |
| 2012/0276063 | A1 | 11/2012 | Meyer et al. |
| 2013/0183714 | A1 | 7/2013 | Osborne et al. |
| 2014/0134674 | A1 | 5/2014 | Pla et al. |
| 2014/0134675 | A1 | 5/2014 | Pla et al. |
| 2014/0206038 | A1 | 7/2014 | Pla et al. |
| 2014/0234905 | A1 | 8/2014 | Pla et al. |
| 2015/0087024 | A1 | 3/2015 | Pla et al. |
| 2015/0093784 | A1 | 4/2015 | Pla et al. |
| 2015/0125905 | A1 | 5/2015 | Pla et al. |
| 2015/0329830 | A1 | 11/2015 | Osborne et al. |
| 2016/0177265 | A1 | 6/2016 | Matsubara et al. |

FOREIGN PATENT DOCUMENTS

| CN | 104560876 A | 4/2015 |
| JP | 6-269283 A | 9/1994 |
| JP | 2004-236607 A | 8/2004 |
| WO | WO 93/01275 A1 | 1/1993 |
| WO | WO 98/30679 A1 | 7/1998 |
| WO | WO 02/088330 A2 | 12/2002 |
| WO | WO 2005/014800 A1 | 2/2005 |
| WO | WO 2005/021704 A2 | 3/2005 |
| WO | WO 2008/033517 A2 | 3/2008 |
| WO | WO 2010/063848 A1 | 6/2010 |
| WO | WO 2013/011093 A1 | 1/2013 |
| WO | WO 2014/208100 A1 | 12/2014 |

OTHER PUBLICATIONS

Extended European Search Report dated Aug. 18, 2018 in Patent Application No. 16773058.9, 7 pages.
Search Report dated Sep. 6, 2018 in Singaporean Patent Application No. 11201707857V, 3 pages.
Written Opinion dated Jun. 21, 2016 in PCT/JP2016/060552 (Submitting English language translation only), 7 pages.
Rebecca I. Erickson, et al."Roles of Insulin and Transferrin in Neural Progenitor Survival and Proliferation", Journal of Neuroscience Research, vol. 86, Issue. 8, 2008, pp. 1884-1894.
Lucas Silvestroff, et al. "Neural and Oligodendrocyte progenitor cells: transferrin effects on cell proliferation", ASN Neuro, vol. 5, Issue. 1, 2013, pp. 43-62.
Luciano Conti, et al. "Niche-Independent Symmetrical Self-Renewal of a Mammalian Tissue Stem Cell", PLoS Biology, vol. 3, Issue. 9, 2005, pp. 1594-1606.
Brent A. Reynolds, et al. "Generation of Neurons and Astrocytes from Isolated Cells of the Adult Mammalian Central Nervous System", Science, vol. 255, issue. 5052, 1992, pp. 1707-1710.

* cited by examiner

*Primary Examiner* — Satyendra K Singh
(74) *Attorney, Agent, or Firm* — Oblon, McClelland, Maier & Neustadt, L.L.P.

(57) ABSTRACT

Culture media, which contain chelated iron, promote cell proliferation of neural stem cells and/or neural progenitor cells while maintaining undifferentiated state and multipotency.

4 Claims, 2 Drawing Sheets

CHELATED IRON-CONTAINING CULTURE MEDIUM FOR NEURAL STEM CELLS

CROSS REFERENCES TO RELATED APPLICATIONS

This application is a continuation of International Patent Application No. PCT/JP2016/060552, filed on Mar. 30, 2016, and claims priority to Japanese Patent Application No. 2015-069978, filed on Mar. 30, 2015, both of which are incorporated herein by reference in their entireties.

BACKGROUND OF THE INVENTION

Field of the Invention

The present invention relates to media for neural stem cells and/or neural progenitor cells. The present invention also relates to culture methods of neural stem cells and/or neural progenitor cells, which comprises using such a medium, and the like.

Discussion of the Background

A neural stem cell is an undifferentiated cell having self-replication competence and multipotency, and is capable of generating various cells in the nervous system (nerve cells and neural progenitor cells, glial cells (astrocytes, oligodendrocytes, etc.), glial progenitor cells and the like). Since neural stem cells and neural progenitor cells can supply cells such as nerve cells and the like that are difficult to proliferate in normal adults, they are drawing attention as a source of biomaterials in regenerative medicine, and are expected to be applicable to the treatment of refractory neurological diseases such as amyotrophic lateral sclerosis, Alzheimer's disease, Parkinson's disease and the like, and, nerve damage. Since treatments of refractory neurological diseases and nerve damage by using such neural stem cells and/or neural progenitor cells, research and development of treatment methods therefor and the like require a large amount of neural stem cells and/or neural progenitor cells, the development and improvement of a culture method of neural stem cells and/or neural progenitor cells in vitro is one of the important objects.

As culture methods of neural stem cells and/or neural progenitor cells, some methods have been reported to date.

Neurosphere culture as an in vitro culture method of neural stem cells is described in Science, 1992, 255(5052), 1707-10, which is incorporated herein by reference in its entirety. This document shows that neural stem cells can be proliferated while maintaining an undifferentiated state of the neural stem cells and maintaining multipotency by culturing the neural stem cells in suspension in a serum-free medium containing epithelial cell proliferation factor (EGF) and basic fibroblast growth factor (bFGF).

As a method of adherent monolayer culture of neural stem cells and/or neural progenitor cells, a method of culturing neural stem cells and/or neural progenitor cells in a medium containing EGF and/or bFGF on an incubator coated with substrates such as laminin, Poly-L-ornithine, fibronectin and the like, and the like can be mentioned (see PLoS Biology, 2005, 3(9), e283, which is incorporated herein by reference in its entirety).

It has been reported that neural stem cells undergo symmetrical division and self-replicate in the above-mentioned adherent monolayer culture, and the culture is advantageous in that it can provide a uniform cell population as compared to neurosphere culture.

While these culture methods are highly advantageous in that they can culture neural stem cells and neural progenitor cells in vitro, they have a disadvantage that cell proliferation is slow and culturing takes time. Therefore, the development of an improved medium and culture conditions for promoting proliferation of neural stem cells and neural progenitor cells while maintaining undifferentiated state and multipotency thereof is desired.

Incidentally, there are some descriptions regarding a medium containing an iron-binding protein. ASN Neuro, 2013, 5(1), e00107, which is incorporated herein by reference in its entirety, reports that apo-transferrin (transferrin not bonded to iron) is important for the proliferation of oligodendrocyte progenitor cells in SVZ which is one region in the neonatal brain of rat. J Neurosci Res, 2008, 86(8), 1884-94, which is incorporated herein by reference in its entirety, reports that apo-transferrin, EGF and FGF2 (bFGF) are important for the neurosphere formation from the embryonic cerebral cortex of rat. Furthermore, it has been reported that the size of neurosphere grows by mixing insulin and apo-transferrin. Moreover, JP-A-6-269283, which is incorporated herein by reference in its entirety, discloses a method using recombinant or fragment of hemoglobin as a substitute for transferrin in a medium for culturing animal cells.

However, an influence of chelated iron on the maintenance of undifferentiated state and multipotency of neural stem cells and promotion of proliferation thereof has not been clarified at all.

Thus, there remains a need for improved media and methods for culturing neural stem cells and/or neural progenitor cells.

SUMMARY OF THE INVENTION

Accordingly, it is one object of the present invention to provide novel media for promoting cell proliferation of neural stem cells and/or neural progenitor cells while maintaining undifferentiated state and multipotency thereof.

It is another object of the present invention to provide novel method of promoting cell proliferation of neural stem cells and/or neural progenitor cells while maintaining undifferentiated state and multipotency thereof.

It is another object of the present invention to provide novel media for inducing neural stem cells and/or neural progenitor cells from pluripotent stem cells and the like.

It is another object of the present invention to provide novel methods for inducing neural stem cells and/or neural progenitor cells from pluripotent stem cells and the like.

These and other objects, which will become apparent during the following detailed description, have been achieved by the inventors' discovery that chelated iron acts to maintain undifferentiated state and multipotency of neural stem cells and promote proliferation thereof, and induces neural stem cells and/or neural progenitor cells from pluripotent stem cells, which resulted in the completion of the present invention.

Thus, the present invention provides:

(1) A medium for neural stem cells and/or neural progenitor cells, comprising chelated iron.

(2) The medium of the above-mentioned (1), which is for promoting proliferation of neural stem cells and/or neural progenitor cells.

(3) The medium of the above-mentioned (1) or (2), which is for maintaining undifferentiation of neural stem cells and/or neural progenitor cells.

(4) The medium of any of the above-mentioned (1) to (3), wherein the neural stem cells and/or neural progenitor cells are derived from pluripotent stem cells.

(5) A medium for inducing neural stem cells and/or neural progenitor cells, which comprises chelated iron.

(6) The medium of the above-mentioned (5), which is for inducing neural stem cells and/or neural progenitor cells from pluripotent stem cells.

(7) The medium of any of the above-mentioned (1) to (6), wherein a content of the chelated iron is 3 to 7 ppb.

(8) The medium of any of the above-mentioned (1) to (7), wherein the chelated iron is bonded to an iron-binding protein.

(9) The medium of any of the above-mentioned (1) to (7), wherein the chelated iron is iron bonded to an iron chelating agent.

(10) The medium of any of the above-mentioned (1) to (7), wherein the chelated iron is iron bonded to at least one kind selected from the group consisting of transferrin, lactoferrin, hemoglobin, ferritin, deferoxamine, citric acid, ethylenediaminetetraacetic acid (EDTA), phytic acid, nitrilotriacetic acid (NTA), diethylenetriaminepentaacetic acid (DTPA), glutamate diacetate (GLDA), hydroxyethylethylenediamineHydroxyethylethylenediamine triacetic acid (HEDTA), glycol etherdiaminetetraacetic acid (GEDTA), triethylenetetramine-N,N,N',N'',N''',N'''-hexaacetic acid (TTHA), hydroxyethyliminodiacetic acid (HIDA), and dihydroxyethylglycine (DHEG).

(11) The medium of the above-mentioned (10), wherein at least one kind of chelated iron is iron bonded to transferrin.

(12) The medium of the above-mentioned (11), wherein a content of transferrin in the medium is not less than 0.5 µg/ml and not more than 6.5 µg/ml.

(13) The medium of the above-mentioned (11), wherein a content of transferrin in the medium is not less than 0.1 µg/ml and not more than 1.8 µg/ml.

(14) The medium of the above-mentioned (10), wherein at least one kind of chelated iron is iron bonded to deferoxamine, citric acid or ethylenediaminetetraacetic acid (EDTA).

(15) The medium of any of the above-mentioned (1) to (14), which is a serum-free medium.

(16) The medium of any of the above-mentioned (1) to (15), comprising a basic fibroblast growth factor (bFGF).

(17) The medium of the above-mentioned (16), wherein an amount of bFGF in the medium is not less than 10 ng/ml and not more than 200 ng/ml.

(18) A method of culturing neural stem cells and/or neural progenitor cells, comprising adding chelated iron to a medium.

(19) A method of proliferating neural stem cells and/or neural progenitor cells, comprising adding chelated iron to a medium.

(20) A method of maintaining undifferentiation of neural stem cells and/or neural progenitor cells, comprising adding chelated iron to a medium.

(21) The method of any of the above-mentioned (18) to (20), wherein the neural stem cells and/or neural progenitor cells are derived from pluripotent stem cells.

(22) A method of inducing neural stem cells and/or neural progenitor cells, comprising adding chelated iron to a medium.

(23) The method of the above-mentioned (22), which is for inducing neural stem cells and/or neural progenitor cells from pluripotent stem cells.

(24) The method of any of the above-mentioned (18) to (23), wherein a content of the chelated iron is 3 to 7 ppb.

(25) The method of any of the above-mentioned (18) to (24), wherein the chelated iron is iron bonded to an iron-binding protein.

(26) The method of any of the above-mentioned (18) to (24), wherein the chelated iron is iron bonded to an iron chelating agent.

(27) The medium of any of the above-mentioned (18) to (24), wherein the chelated iron is iron bonded to at least one kind selected from the group consisting of transferrin, lactoferrin, hemoglobin, ferritin, deferoxamine, citric acid, ethylenediaminetetraacetic acid (EDTA), phytic acid, nitrilotriacetic acid (NTA), diethylenetriaminepentaacetic acid (DTPA), glutamate diacetate (GLDA), hydroxyethylethylenediamineHydroxyethylethylenediamine triacetic acid (HEDTA), glycol etherdiaminetetraacetic acid (GEDTA), triethylenetetramine-N,N,N',N'',N''',N'''-hexaacetic acid (TTHA), hydroxyethyliminodiacetic acid (HIDA), and dihydroxyethylglycine (DHEG).

(28) The method of the above-mentioned (27), wherein at least one kind of chelated iron is iron bonded to transferrin.

(29) The method of the above-mentioned (28), wherein a content of transferrin in the medium is not less than 0.5 µg/ml and not more than 6.5 µg/ml.

(30) The method of the above-mentioned (28), wherein a content of transferrin in the medium is not less than 0.1 µg/ml and not more than 1.8 µg/ml.

(31) The method of the above-mentioned (27), wherein at least one kind of chelated iron is iron bonded to deferoxamine, citric acid or ethylenediaminetetraacetic acid (EDTA).

(32) A culture composition comprising the medium of any of the above-mentioned (1) to (17) and neural stem cells and/or neural progenitor cells.

Effect of the Invention

According to the present invention, neural stem cells and/or neural progenitor cells can be efficiently cultured for a long term while maintaining an undifferentiated state and multipotency. According to the present invention, moreover, neural stem cells and/or neural progenitor cells can be efficiently induced. As a result, a large amount of neural stem cells and/or neural progenitor cells can be obtained by culturing. In addition, the cost necessary for culturing neural stem cells and/or neural progenitor cells can be reduced.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The present invention provides a medium for promoting cell proliferation of neural stem cells and/or neural progenitor cells while maintaining undifferentiated state and multipotency, as well as a medium for improving induction efficiency of neural stem cells and/or neural progenitor cells from pluripotent stem cells and the like (hereinafter these are to be also collectively-referred to as the medium of the present invention). The present invention further provides a method of efficiently culturing neural stem cells and/or neural progenitor cells for a long term while maintaining undifferentiated state and multipotency, and suppressing differentiation, as well as a method of efficiently inducing neural stem cells and/or neural progenitor cells from pluripotent stem cells and the like (hereinafter these are to be also collectively referred to as the method of the present invention).

(1) Chelated Iron

In the present specification, the chelated iron refers to iron bonded to an iron chelating agent, or iron bonded to an iron-binding protein.

Chelate is bonding (coordination) of a ligand having plural coordination positions (multidentate ligand) to metal ion(s). Chelation means that two or more coordinating atoms that a ligand has coordinate to one ion or atom to form a cyclic compound. Coordination means donation of electrons from an electron-pair donor to an electron-pair acceptor, and the bond formed by coordination is called a coordinate bond. Ligands refer to compounds that coordinate to metals. Ligands have a group having a lone pair of electrons, and this group coordinates to a metal. Of the ligands, ligands having plural coordinating groups are called multidentate ligands. Coordination atom refers to an atom directly bonded to a metal, among the elements constituting the ligand.

A chelate complex refers to a cyclic compound formed by bonding of a multidentate ligand and a metal. A chelate complex does not easily separate from coordinated substances since the ligand has plural coordinating groups.

A substance capable of forming a complex with iron and other than proteins is called an iron chelating agent, and a protein capable of forming a complex with iron is called an iron-binding protein.

In the present specification, iron bonded to an iron chelating agent and iron bonded to an iron-binding protein mean iron forming an iron chelate complex with an iron chelating agent, and iron forming an iron chelate complex with an iron-binding protein, respectively.

Chelated iron used in the present invention may be iron bonded to an iron chelating agent or iron bonded to an iron-binding protein, or a combination of iron bonded to an iron chelating agent and iron bonded to an iron-binding protein. The chelated iron to be used in the present invention may be composed of one kind of chelated iron, or plural kinds of chelated irons.

In one embodiment of the present invention, chelated iron is provided in a medium by adding an iron chelate complex to the medium. In another embodiment, chelated iron is provided in a medium by adding each of an iron chelating agent or iron-binding protein, which has not formed a complex with iron, and a source of iron to the medium. In the present specification, a source of iron refers to iron which has not foamed a complex, and capable of forming a complex with an iron chelating agent or iron-binding protein. The source of iron is not particularly limited as long as desired effects such as promotion of proliferation and maintenance of undifferentiated state of neural stem cells and/or neural progenitor cells and the like can be achieved, and may be ferrous, $Fe^{2+}$ or ferric, $Fe^{3+}$. When an iron chelating agent or iron-binding protein, and a source of iron are separately added to a medium, the source of iron is preferably water-soluble. Examples of the source of iron include, but are not limited to, iron sulfate, iron chloride, potassium hexacyanoferrate. The iron chelating agent or iron-binding protein, and a source of iron may be simultaneously added or separately added as long as the desired effects such as promotion of proliferation and maintenance of undifferentiated state of neural stem cells and/or neural progenitor cells and the like can be achieved. In addition, chelated iron can be provided by a source of iron originally contained in the medium, and an iron chelating agent or iron-binding protein added thereto. In a preferable embodiment, chelated iron is provided in a medium by forming a complex of iron chelating agent or iron-binding protein, and a source of iron in advance, and adding the complex to the medium.

When an iron chelating agent or iron-binding protein, and a source of iron are separately added to a medium, the amount of the iron chelating agents or iron-binding proteins, and the amount of a source of iron to be added to the medium of the present invention are not particularly limited as long as the desired effects such as promotion of proliferation and maintenance of undifferentiated state of neural stem cells and/or neural progenitor cells and the like can be achieved. They can be adjusted to set the amount of the chelated iron in the medium to 3 to 7 ppb, preferably 4 to 6 ppb.

When a complex is formed in advance from an iron chelating agent or iron-binding protein, and a source of iron, and added to the complex medium, the amount of the chelated iron to be contained in the medium of the present invention is not particularly limited as long as the desired effects such as promotion of proliferation and maintenance of undifferentiated state of neural stem cells and/or neural progenitor cells and the like can be achieved. It is 3 to 7 ppb, preferably 4 to 6 ppb. The amount of the chelated iron in the medium can be measured according to a method known per se, for example, mass spectrometry and the like. The amount of the chelated iron in the medium can be measured by, for example, measuring the amount of iron of a high molecular form by using an inductively coupled plasma-mass spectrometry apparatus according to the method described in the Examples.

When the amount of the chelated iron in the medium is too small, proliferation of neural stem cells and/or neural progenitor cells is not promoted. When the amount of the chelated iron in the medium is too high, proliferation of neural stem cells and/or neural progenitor cells is not promoted.

Examples of the iron chelating agent include deferoxamine, citric acid, ethylenediaminetetraacetic acid (EDTA), phytic acid, nitrilotriacetic acid (NTA), diethylenetriaminepentaacetic acid (DTPA), glutamate diacetate (GLDA), hydroxyethylethylenediamineHydroxyethylethylenediamine triacetic acid (HEDTA; hydroxyethylethylenediamine triacetic acid), glycol ether diamine tetraacetic acid (GEDTA), triethylenetetramine-N,N,N',N",N'",N"'-hexaacetic acid (TTHA), hydroxyethyl imino diacetic acid (HIDA), dihydroxyethyl glycine (DHEG) and the like.

When deferoxamine (N-(5-aminopentyl)-N-hydroxy-N'-[5-(N-hydroxy-3-{[5-(N-hydroxyacetamido)pentyl]carbamoyl}-propanamido)pentyl]butanediamide) is used as an iron chelating agent, deferoxamine includes deferoxamine and a salt thereof, and deferoxamine derivative and a salt thereof.

As a method of obtaining deferoxamine, for example, it can be obtained by culturing deferoxamine B producing strain belonging to the genus *Streptomyces*, for example, *Streptomyces pilosus*; JCM4403, ATCC19797 and the like, or can also be synthesized by the method of Proleg et al (Helv Chim Acta, 45,31,1962, which is incorporated herein by reference in its entirety).

Examples of the deferoxamine derivative include formaldehydedeferoxamine, acetamidodeferoxamine, propylamidedeferoxamine, butylamidedeferoxamine, benzoylamidedeferoxamine, succinamidedeferoxamine, methylsulfoamidedeferoxamine (Ihnat et al, J. Pharm Sci. 91: 1733-1741 (2002), which is incorporated herein by reference in its entirety), hydroxyethylstarchdeferoxamine (Pedchenko et al, J. Neuroimmunol. 84: 188-197 (1998), which is incorporated herein by reference in its entirety), aminooxyacetyl-ferrioxamine (Pochon et al, Int. J. Cancer. 43: 1188-1194 (1989), which is incorporated herein by reference in its entirety)) and the like.

Examples of the salt of deferoxamine are not particularly limited as long as the desired effects such as promotion of proliferation and maintenance of undifferentiated state of neural stem cells and/or neural progenitor cells and the like can be achieved. For example, deferoxamine mesylate salt (CAS No. 138-14-7), and deferoxamine hydrochloride (CAS No. 1950-39-6) can be mentioned. Deferoxamine mesylate salt may be commercially available from Novartis Pharma etc.

When deferoxamine is used as an iron chelating agent, the concentration of deferoxamine contained in the medium is not particularly limited as long as the desired effects such as promotion of proliferation and maintenance of undifferentiated state of neural stem cells and/or neural progenitor cells and the like can be achieved. When it is too high, the cell cycle of neural stem cells and/or neural progenitor cells is inhibited and differentiation is promoted. Thus, it is generally not more than about 25 µg/ml, preferably not more than about 10 µg/ml, more preferably not more than 10 µg/ml. When it is too small, the desired effects cannot be obtained. Therefore, it is generally not less than about 0.1 µg/ml, preferably not less than about 1 µg/ml, more preferably not less than 1 µg/ml. The concentration range of deferoxamine in the medium is about 0.1 to 25 µg/ml, preferably about 1 to 10 µg/ml, more preferably 1 to 10 µg/ml. In the present specification, "about" is used to mean that ±10% is tolerable.

When citric acid is used as an iron chelating agent, the citric acid includes citric acid and a salt thereof. Citric acid is a well-known compound, and can be obtained by a method known per se. When citric acid is used as an iron chelating agent, examples of the iron chelate complex of the present include ferric citrate, ammonium ferric citrate, sodium ferrous citrate and the like. Ammonium ferric citrate is a known compound and can be produced, for example, by adding iron(III) hydroxide to an aqueous solution of citric acid and ammonia. Ferric citrate, ammonium ferric citrate and sodium ferrous citrate may be commercially available from Sigma-Aldrich Co. LLC etc.

When citric acid is used as an iron chelating agent, the concentration of citric acid contained in the medium is not particularly limited as long as the desired effects such as promotion of proliferation and maintenance of undifferentiated state of neural stem cells and/or neural progenitor cells and the like can be achieved. It is generally not more than about 30 µg/ml, preferably not more than about 3 µg/ml, more preferably not more than 3 µg/ml. When it is too low, the desired effects cannot be afforded. Thus, it is generally not less than about 0.03 µg/ml, preferably not less than about 0.3 µg/ml, more preferably not less than 0.3 µg/ml. The concentration range of citric acid in the medium is about 0.03 to 30 µg/ml, preferably about 0.3 to 3 µg/ml, more preferably 0.3 to 3 µg/ml.

When ethylenediaminetetraacetic acid (EDTA) is used as an iron chelating agent, EDTA includes EDTA and a salt thereof. EDTA is a well-known compound, and can be obtained by a method known per se.

As the salt of EDTA, sodium salts such as EDTA 2Na, EDTA 3Na, EDTA 4Na and the like, potassium salts such as EDTA 2K, EDTA 3K and the like, magnesium salt, chromate, sodium calcium salt and the like can be mentioned. The salt of EDTA to be used in the present invention is not particularly limited as long as the desired effects such as promotion of proliferation and maintenance of undifferentiated state of neural stem cells and/or neural progenitor cells and the like can be achieved. However, from the aspects of easy availability and the like, it is preferably sodium salt or potassium salt.

When EDTA is used as an iron chelating agent, the concentration of EDTA contained in the medium is not particularly limited as long as the desired effects such as promotion of proliferation and maintenance of undifferentiated state of neural stem cells and/or neural progenitor cells and the like can be achieved. It is generally not more than about 50 µg/ml, preferably not more than about 5 µg/ml, more preferably not more than 5 µg/ml. When it is too low, the desired effects cannot be obtained. Thus, it is generally not less than about 0.05 µg/ml, preferably not less than about 0.5 µg/ml, more preferably not less than 0.5 µg/ml. The concentration range of EDTA in the medium is about 0.05 to 50 µg/ml, preferably about 0.5 to 5 µg/ml, more preferably 0.5 to 5 µg/ml.

When phytic acid; myo-inositol-1,2,3,4,5,6-penta-phosphoric acid) (CAS No. 83-86-3) is used as an iron chelating agent, it includes phytic acid and a salt thereof. Phytic acid is a well-known compound, and can be obtained by a method known per se.

When phytic acid is used as an iron chelating agent, the concentration of phytic acid contained in the medium is not particularly limited as long as the desired effects such as promotion of proliferation and maintenance of undifferentiated state of neural stem cells and/or neural progenitor cells and the like can be achieved. It is generally not more than about 120 µg/ml, preferably not more than about 12 µg/ml, more preferably not more than 12 µg/ml. When it is too low, the desired effects cannot be obtained. Thus, it is generally not less than about 0.12 µg/ml, preferably not less than about 1.2 µg/ml, more preferably not less than 1.2 µg/ml. The concentration range of phytic acid in the medium is about 0.12 to 120 µg/ml, preferably about 1.2 to 12 µg/ml, preferably 1.2 to 12 µg/ml.

When nitrilotriacetic acid (NTA) is used as an iron chelating agent, for example, it includes nitrilotriacetic acid and a salt thereof. Nitrilotriacetic acid is a known compound, and can be obtained by a method known per se. In addition, a commercially available nitrilotriacetic acid such as NTA.3H (CAS No. 139-13-9) sold by CHELEST Corporation and the like can also be used.

Examples of the salt of nitrilotriacetic acid include, but are not limited to, NTA.H.2Na (CAS No. 15467-20-6), NTA 3Na H$_2$O (CAS No. 5064-31-3), NTA H 2(NH$_4$). CHELEST 3NTB(NTA.H.2Na), CHELEST NTA(NTA.3Na.H$_2$O), CHELEST 2NTA(NTA.3Na.H$_2$O), CHELEST 2NX-40 (NTA.H.2(NH$_4$)) and the like sold by CHELEST Corporation can also be used.

When NTA is used as an iron chelating agent, the concentration of NTA contained in the medium is not particularly limited as long as the desired effects such as promotion of proliferation and maintenance of undifferentiated state of neural stem cells and/or neural progenitor cells and the like can be achieved. It is generally not more than about 30 µg/ml, preferably not more than about 3 µg/ml, more preferably not more than 3 µg/ml. When it is too low, the desired effects cannot be obtained. Thus, it is generally not less than about 0.03 µg/ml, preferably not less than about 0.3 µg/ml, more preferably not less than 0.3 µg/ml. The concentration range of NTA in the medium is about 0.03 to 30 µg/ml, preferably about 0.3 to 3 µg/ml, more preferably 0.3 to 3 µg/ml.

When DTPA is used as an iron chelating agent, DTPA includes DTPA and a salt thereof, and DTPA derivative and a salt thereof. DTPA is a known compound, and can be obtained by a method known per se.

Examples of the derivative of DTPA include non-ester bond-DTPA derivative (JP-A-Hei9-031037), tetra-alkyl group-DTPA (JP-A-2006-342105) and the like.

Examples of the salt of DTPA include, but are not limited to, sodium salt. The salt of DTPA to be used in the present invention is not particularly limited as long as the desired effects such as promotion of proliferation and maintenance of undifferentiated state of neural stem cells and/or neural progenitor cells and the like can be achieved. However, from the aspects of easy availability and the like, it is preferably sodium salt.

When DTPA is used as an iron chelating agent, the concentration of DTPA contained in the medium is not particularly limited as long as the desired effects such as promotion of proliferation and maintenance of undifferentiated state of neural stem cells and/or neural progenitor cells and the like can be achieved. It is generally not more than about 40 µg/ml, preferably not more than about 4 µg/ml, more preferably not more than 4 µg/ml. When it is too low, the desired effects cannot be obtained. Thus, it is generally not less than about 0.04 µg/ml, preferably not less than about 0.4 µg/ml, more preferably not less than 0.4 µg/ml. The concentration range of DTPA in the medium is about 0.04 to 40 µg/ml, preferably about 0.4 to 4 µg/ml, more preferably 0.4 to 4 µg/ml.

When GLDA is used as an iron chelating agent, GLDA includes GLDA and a salt thereof, and GLDA derivative and a salt thereof. GLDA is a well-known compound, and can be obtained by a method known per se. For example, GLDA can be synthesized by the methods described in JP-A-hei-6-59422, U.S. Pat. No. 2,500,019, which are incorporated herein by reference in their entireties, and the like.

As the salt of GLDA, alkali metal salts such as sodium salt and the like, ammonium salt, amine salt and the like can be mentioned. It is not particularly limited as long as the desired effects such as promotion of proliferation and maintenance of undifferentiated state of neural stem cells and/or neural progenitor cells and the like can be achieved. However, from the aspects of easy availability and the like, the salt of GLDA is preferably sodium salt.

When GLDA is used as an iron chelating agent, the concentration of GLDA contained in the medium is not particularly limited as long as the desired effects such as promotion of proliferation and maintenance of undifferentiated state of neural stem cells and/or neural progenitor cells and the like can be achieved. It is generally not more than about 50 µg/ml, preferably not more than about 5 µg/ml, more preferably not more than 5 µg/ml. When it is too low, the desired effects cannot be obtained. Thus, it is generally not less than about 0.05 µg/ml, preferably not less than about 0.5 µg/ml, more preferably not less than 0.5 µg/ml. The concentration range of GLDA in the medium is about 0.05 to 50 µg/ml, preferably about 0.5 to 5 µg/ml, more preferably 0.5 to 5 µg/ml.

When HEDTA is used as an iron chelating agent, HEDTA includes HEDTA and a salt thereof, and HEDTA derivative and a salt thereof. HEDTA is a well-known compound, and can be obtained by a method known per se.

As the salt of HEDTA, sodium salt and the like can be mentioned. It is not particularly limited as long as the desired effects such as promotion of proliferation and maintenance of undifferentiated state of neural stem cells and/or neural progenitor cells and the like can be achieved. However, from the aspects of easy availability and the like, the salt of HEDTA is preferably trisodium salt (CAS No. 139-89-9).

When HEDTA is used as an iron chelating agent, the concentration of HEDTA contained in the medium is not particularly limited as long as the desired effects such as promotion of proliferation and maintenance of undifferentiated state of neural stem cells and/or neural progenitor cells and the like can be achieved. It is generally not more than about 50 µg/ml, preferably not more than about 5 µg/ml, more preferably not more than 5 µg/ml. When it is too low, the desired effects cannot be obtained. Thus, it is generally not less than about 0.05 µg/ml, preferably not less than about 0.5 µg/ml, more preferably not less than 0.5 µg/ml. The concentration range of HEDTA in the medium is about 0.05 to 50 µg/ml, preferably about 0.5 to 5 µg/ml, more preferably 0.5 to 5 µg/ml.

When GEDTA is used as an iron chelating agent, GEDTA includes GEDTA and a salt thereof, and GEDTA derivative and a salt thereof. GEDTA is a well-known compound, and can be obtained by a method known per se.

As the salt of GEDTA, potassium salt, sodium salt and the like can be mentioned. Examples of the derivative of GEDTA include 8-amino-2-[(2-amino-5-methylphenoxy)methyl]-6-methoxyquinoline-N,N,N',N'-tetraacetic acid (Org Biomol Chem. 2008 Jul. 7; 6(13):2361-8, which is incorporated herein by reference in its entirety). It is not particularly limited as long as the desired effects such as promotion of proliferation and maintenance of undifferentiated state of neural stem cells and/or neural progenitor cells and the like can be achieved. However, from the aspects of easy availability and the like, the salt of GEDTA is preferably sodium salt.

When GEDTA is used as an iron chelating agent, the concentration of GEDTA contained in the medium is not particularly limited as long as the desired effects such as promotion of proliferation and maintenance of undifferentiated state of neural stem cells and/or neural progenitor cells and the like can be achieved. It is generally not more than about 50 µg/ml, preferably not more than about 5 µg/ml, more preferably not more than 5 µg/ml. When it is too low, the desired effects cannot be obtained. Thus, it is generally not less than about 0.05 µg/ml, preferably not less than about 0.5 µg/ml, more preferably not less than 0.5 µg/ml. The concentration range of GEDTA in the medium is about 0.05 to 50 µg/ml, preferably about 0.5 to 5 µg/ml, more preferably 0.5 to 5 µg/ml.

When TTHA is used as an iron chelating agent, TTHA includes TTHA and a salt thereof, and TTHA derivative and a salt thereof. TTHA is a well-known compound, and can be obtained by a method known per se.

As the salt of TTHA, sodium salt and the like can be mentioned. It is not particularly limited as long as the desired effects such as promotion of proliferation and maintenance of undifferentiated state of neural stem cells and/or neural progenitor cells and the like can be achieved. However, from the aspects of easy availability and the like, the salt of TTHA is preferably sodium salt.

When TTHA is used as an iron chelating agent, the concentration of TTHA contained in the medium is not particularly limited as long as the desired effects such as promotion of proliferation and maintenance of undifferentiated state of neural stem cells and/or neural progenitor cells and the like can be achieved. It is generally not more than about 110 µg/ml, preferably not more than about 11 µg/ml, more preferably not more than 11 µg/ml. When it is too low, the desired effects cannot be obtained. Thus, it is generally not less than about 0.11 µg/ml, preferably not less than about 1.1 µg/ml, more preferably not less than 1.1 µg/ml. The concentration range of TTHA in the medium is about 0.11 to 110 µg/ml, preferably about 1.1 to 11 µg/ml, more preferably 1.1 to 11 µg/ml.

When HIDA is used as an iron chelating agent, HIDA includes HIDA and a salt thereof, and HIDA derivative and a salt thereof. HIDA is a well-known compound, and can be obtained by a method known per se.

As the salt of HIDA, sodium salt and the like can be mentioned. It is not particularly limited as long as the desired effects such as promotion of proliferation and maintenance of undifferentiated state of neural stem cells and/or neural progenitor cells and the like can be achieved. However, from the aspects of easy availability and the like, the salt of HIDA is preferably disodium salt.

When HIDA is used as an iron chelating agent, the concentration of HIDA contained in the medium is not particularly limited as long as the desired effects such as promotion of proliferation and maintenance of undifferentiated state of neural stem cells and/or neural progenitor cells and the like can be achieved. It is generally not more than about 30 µg/ml, preferably not more than about 3 µg/ml, more preferably not more than 3 µg/ml. When it is too low, the desired effects cannot be obtained. Thus, it is generally not less than about 0.03 µg/ml, preferably not less than about 0.3 µg/ml, more preferably not less than 0.3 µg/ml. The concentration range of HIDA in the medium is about 0.03 to 30 µg/ml, preferably about 0.3 to 3 µg/ml, more preferably 0.3 to 3 µg/ml.

When DHEG is used as an iron chelating agent, DHEG includes DHEG and a salt thereof, and DHEG derivative and a salt thereof. DHEG is a well-known compound, and can be obtained by a method known per se.

As the salt of DHEG, sodium salt and the like can be mentioned. It is not particularly limited as long as the desired effects such as promotion of proliferation and maintenance of undifferentiated state of neural stem cells and/or neural progenitor cells and the like can be achieved. However, from the aspects of easy availability and the like, the salt of DHEG is preferably sodium salt.

When DHEG is used as an iron chelating agent, the concentration of DHEG contained in the medium is not particularly limited as long as the desired effects such as promotion of proliferation and maintenance of undifferentiated state of neural stem cells and/or neural progenitor cells and the like can be achieved. It is generally not more than about 30 µg/ml, preferably not more than about 3 µg/ml, more preferably not more than 3 µg/ml. When it is too low, the desired effects cannot be obtained. Thus, it is generally not less than about 0.03 µg/ml, preferably not less than about 0.3 µg/ml, more preferably not less than 0.3 µg/ml. The concentration range of DHEG in the medium is about 0.03 to 30 µg/ml, preferably about 0.3 to 3 µg/ml, more preferably 0.3 to 3 µg/ml.

Examples of the iron-binding protein include, but are not limited to, transferrin, lactoferrin, hemoglobin, ferritin and the like. Preferably, an iron-binding protein is transferrin, lactoferrin, hemoglobin or ferritin. An iron-binding protein may be a fragment containing an iron-binding site. An iron-binding protein can be obtained by a method known per se.

An iron-binding protein to be used in the present invention is, for example, iron-binding proteins derived from rodents such as mouse, rat, hamster, guinea pig and the like, lagomorpha such as rabbit and the like, ungulata such as swine, bovine, goat, horse, sheep and the like, carnivora such as canine, feline and the like, primates such as human, monkey, cynomolgus monkey, marmoset, orangutan, chimpanzee and the like, and the like, preferably, iron-binding proteins derived from an animal allogeneic with the neural stem cells and/or neural progenitor cells to be cultured.

An iron-binding protein to be used in the present invention may be natural iron-binding proteins, or may be non-natural. The iron-binding protein may be an iron-binding protein obtained by isolating and purifying an iron-binding protein expressed from a gene naturally owned by living organisms, viable cells and the like, or a recombinant iron-binding protein isolated and purified from those produced by microorganisms, cells, animals and, plants and the like by gene recombination technology.

When transferrin is, used as an iron-binding protein, chelated iron is preferably provided in the medium as holotransferrin which is an iron chelate complex in which transferrin and iron are bonded. Transferrin bonded to iron is called holotransferrin, and transferrin not bonded to iron is called apotransferrin.

In the present specification, holotransferrin includes a molecule in which 1 molecule of apotransferrin and one iron ion are bonded, and a molecule in which 1 molecule of apotransferrin and two iron ions are bonded.

In the present specification, a molecule in which 1 molecule of apotransferrin and one iron ion are bonded, and a molecule in which 1 molecule of apotransferrin and two iron ions are bonded are collectively referred to as iron-laden transferrin. Since it is difficult to strictly distinguish iron-laden transferrin from apotransferrin without bonding to iron in a solution such as a medium and the like, a mixture of the above-mentioned iron-laden transferrin and apotransferrin without bonding to iron is also referred to as, according to the practice in the technical field, holotransferrin also in the present specification.

In the present invention, an iron content of holotransferrin is 200 µg/g to 1400 µg/g. The iron content of holotransferrin is not particularly limited as long as the desired effects such as promotion of proliferation and maintenance of undifferentiated state of neural stem cells and/or neural progenitor cells and the like can be achieved. Generally, however, from the aspects of easy availability and the like, it is preferably 200 μg/g to 500 μg/g. The iron content is more preferably 200 μg/g to 500 μg/g, since it is close to that of transferrin and iron in serum.

As the nucleic acid sequence encoding human transferrin, NM_001063 (NCBI Accession No.) can be mentioned; as the amino acid sequence of human transferrin, NP_001054 can be mentioned, but the sequences are not limited thereto.

When holotransferrin is used as an iron chelate complex, the concentration of holotransferrin contained in the medium is not particularly limited as long as the desired effects can be achieved. The concentration of holotransferrin is preferably one that sets the amount of chelated iron in the medium to 3 to 7 ppb, preferably 4 to 6 ppb. Specifically, the concentration of holotransferrin in the medium is as follows.

When holotransferrin is used as an iron chelate complex, the concentration of transferrin contained in the medium can be appropriately increased or decreased according to the iron content of holotransferrin to be used, and is not particularly limited as long as the desired effects such as promotion of proliferation and maintenance of undifferentiated state of neural stem cells and/or neural progenitor cells and the like can be achieved. It is generally 0.1 to 6.5 μg/ml, more preferably 0.3 to 6.5 μg/ml, preferably 0.5 to 6.5 μg/ml, further preferably 1 to 5 μg/ml, further more preferably 2.5 to 5 μg/ml. The "concentration of transferrin contained in the medium" (or "content of transferrin in the medium") refers to a total of the concentration of iron-laden transferrin and the concentration of apo-transferrin without bonding to iron ion in the medium.

More particularly, when holotransferrin having a high iron content (e.g., iron content of 1100 to 1400 μg/g) is used, the desired effects such as promotion of proliferation and maintenance of undifferentiated state of neural stem cells and/or neural progenitor cells and the like can be achieved even by using transferrin at a concentration lower than the above-mentioned value. The concentration is generally not more than 2.0 μg/ml, preferably not more than 1.8 μg/ml, more preferably not more than 1.4 μg/ml, further preferably not more than 1.3 μg/ml. When it is too low, the desired effects cannot be obtained. Thus, it is generally not less than 0.1 μg/ml, preferably not less than 0.2 μg/ml, more preferably not less than 0.3 μg/ml. When transferrin having a high iron content (e.g., iron content of 1100 to 1600 μg/g) is used, the concentration range of transferrin in the medium is 0.1 to 2.0 μg/ml, preferably 0.1 to 1.8 μg/ml, further preferably 0.2 to 1.4 μg/ml, further more preferably 0.3 to 1.3 μg/ml.

On the other hand, when holotransferrin having a low iron content (e.g., iron content of 200 to 500 μg/g) such as holotransferrin isolated from serum and the like is used, the amount of transferrin in the medium is generally not more than about 6.5 μg/ml, preferably not more than about 5 μg/ml, more preferably not more than 5 μg/ml. When it is too low, the desired effects cannot be obtained. Thus, it is generally not less than about 0.5 μg/ml, preferably not less than about 1 μg/ml, more preferably not less than 1 μg/ml, further preferably not less than about 2.5 μg/ml, further more preferably not less than 2.5 μg/ml. For example, when holotransferrin having a low iron content (e.g., iron content of 200 to 500 μg/g) is used, the concentration range of transferrin in the medium is 0.5 to 6.5 μg/ml, preferably about 1 to 5 μg/ml, preferably 1 to 5 μg/ml, further preferably about 2.5 to 5 μg/ml, further more preferably 2.5 to 5 μg/ml.

While the desired amount of chelated iron in the medium is afforded by achieving the above-mentioned conditions, but the conditions are not limited thereto.

The iron content of holotransferrin can be measured, for example, by suspending holotransferrin in a suitable solvent, measuring the amount of iron of a high molecular form in the solvent by SEC-ICP-MS, and calculating the amount of iron per 1 g of transferrin protein.

For example, when holotransferrin is used as the above-mentioned iron chelate complex, a commercially available reagent (Sigma Aldrich) can be used.

When lactoferrin is used as an iron-binding protein, M83202, M93150, U07643 can be mentioned as a nucleic acid sequence encoding human lactoferrin, and AAA59511 can be mentioned as an amino acid sequence of human lactoferrin, but the sequences are not limited thereto.

When lactoferrin is used as an iron-binding protein, the concentration of lactoferrin contained in the medium is not particularly limited as long as the desired effects such as promotion of proliferation and maintenance of undifferentiated state of neural stem cells and/or neural progenitor cells and the like can be achieved. It is generally not more than about 10 μg/ml, preferably not more than about 5 μg/ml, more preferably not more than 5 μg/ml. When it is too low, the desired effects cannot be obtained. Thus, it is generally not less than about 1 μg/ml, preferably not less than about 2.5 μg/ml, more preferably not less than 2.5 μg/ml. The concentration range of lactoferrin in the medium is about 1 to 10 μg/ml, preferably about 2.5 to 5 μg/ml, preferably 2.5 to 5 μg/ml.

When hemoglobin is used as an iron-binding protein, hemoglobin may be a monomer of α subunit, β subunit, ε subunit, γ subunit (γ-G subunit or γ-A subunit), or δ subunit, a tetramer constituted of two α subunits and two β subunits, a tetramer constituted of two α subunits and two δ subunits or the like. In addition, hemoglobin may be oxyhemoglobin bonding to oxygen, or deoxyhemoglobin without bonding to oxygen (reduced hemoglobin).

Examples of the nucleic acid sequence encoding hemoglobin a subunit include, but are not limited to, NM_000558 and NM_000517, and examples of the amino acid sequence of human hemoglobin a subunit include, but are not limited to, NP_000549 and NP_000508.

Examples of the nucleic acid sequence encoding hemoglobin β subunit include, but are not limited to, NM_000518, and examples of the amino acid sequence of human hemoglobin β subunit include, but are not limited to, NP_000509.

Examples of the nucleic acid sequence encoding hemoglobin δ subunit include, but are not limited to, NM_000519, and examples of the amino acid sequence of human hemoglobin δ subunit include, but are not limited to, NP_000510.

Examples of the nucleic acid sequence encoding hemoglobin γ subunit include, but are not limited to, NM_000184, and examples of the amino acid sequence of human hemoglobin γ subunit include, but are not limited to, NP_000175.

When hemoglobin is used as an iron-binding protein, the concentration of hemoglobin contained in the medium is not particularly limited as long as the desired effects such as promotion of proliferation and maintenance of undifferentiated state of neural stem cells and/or neural progenitor cells and the like can be achieved. It is generally not more than about 8 μg/ml, preferably not more than about 4.8 μg/ml, more preferably not more than 4.8 μg/ml. When it is too low, the desired effects cannot be obtained. Thus, it is generally not less than about 0.8 μg/ml, preferably not less than about 3.2 μg/ml, more preferably not less than 3.2 μg/ml. The concentration range of hemoglobin in the medium is about, 0.8 to 8 μg/ml, preferably about 3.2 to 4.8 μg/ml, preferably 3.2 to 4.8 μg/ml.

When ferritin is used as an iron-binding protein, examples of the nucleic acid sequence encoding human ferritin include, but are not limited to, NM_000146 (light chain), NM_002032 (heavy chain) and NM_177478 (mitochondria), and examples of the amino acid sequence of human ferritin include, but are not limited to, NP_000137 (light chain), NP_002023 (heavy chain) and NP_803431 (mitochondria).

When ferritin is used as an iron-binding protein, the concentration of ferritin contained in the medium is not particularly limited as long as the desired effects such as promotion of proliferation and maintenance of undifferentiated state of neural stem cells and/or neural progenitor cells and the like can be achieved. It is generally not more than about 50 µg/ml, preferably not more than about 30 µg/ml, more preferably not more than 30 µg/ml. When it is too low, the desired effects cannot be obtained. Thus, it is generally not less than about 5 µg/ml, preferably not less than about 20 µg/ml, more preferably not less than 20 µg/ml. The concentration range of ferritin in the medium is about 5 to 50 µg/ml, preferably about 20 to 30 µg/ml, more preferably 20 to 30 µg/ml.

(2) Neural Stem Cells and/or Neural Progenitor Cells

In the present specification, neural stem cell means an undifferentiated cell maintaining multipotency into nervous system cells (nerve cells and glial cells (astrocytes, oligodendrocytes and the like), and progenitor cells thereof), and having self-replication competence. Specifically, neural stem cell is a cell having an ability to finally produce nerve cells and glial cells (astrocytes, oligodendrocytes and the like), which does not substantially produce cells other than the nervous system such as epidermal system cells, blood-lineage cells, myocytes and the like unless a special operation such as reprogramming and the like is applied. By substantially not producing means that not less than 90% of the cells produced by neural stem cells are either nerve cells and glial cells (astrocytes, oligodendrocytes and the like), or progenitor cells thereof.

In the present specification, a neural progenitor cell is an undifferentiated cell having a division potential, and capable of finally differentiating into one or more kinds of nerve cells. The neural progenitor cell refers to a cell destined to finally produce a nerve cell, which does not substantially produce anything other than nerve cells and progenitor cells thereof. A glial progenitor cell is an undifferentiated cell derived from a neural stem cell, which has a division potential, is capable of differentiating into any of astrocyte, oligodendrocyte, microglia, ependymal cell and Schwann cell, or progenitor cell thereof, and does not substantially differentiate into a nerve cell.

Since it is difficult to strictly distinguish neural stem cell from neural progenitor cell, they may be used without distinction as "neural stem cells and/or neural progenitor cells" in the present specification.

In the present invention, neural stem cells and/or neural progenitor cells derived from mammals are generally used. Examples of the mammals include, but are not limited to, rodents such as mouse, rat, hamster, guinea pig and the like, lagomorpha such as rabbit and the like, ungulata such as swine, bovine, goat, horse, sheep and the like, carnivora such as canine, feline and the like, primates such as human, monkey, cynomolgus monkey, marmoset, orangutan, chimpanzee and the like, and the like. The neural stem cells and/or neural progenitor cells to be used in the present invention are preferably neural stem cells and/or neural progenitor cells of rodents such as mouse and the like or primates such as human and the like, more preferably human neural stem cells and/or human neural progenitor cells.

Examples of the neural stem cells and/or neural progenitor cells to be used in the present invention include those derived from pluripotent stem cells, those separated from biological tissues, those directly induced to differentiate from fibroblasts and the like without intervention of pluripotent stem cells (Stem Cells. 2012 June; 30(6):1109-19, which is incorporated herein by reference in its entirety) and the like, and are not particularly limited as long as they maintain undifferentiated state described above, maintain multipotency and maintain an ability to produce nerve cell. In the present specification, a pluripotent stem cell means an immature cell having self-replication competence and differentiation/proliferative capacity, which is a cell capable of differentiating into any tissue or cell constituting living organisms, except placenta. Examples of the pluripotent stem cell include embryonic stem cell (ES cell), induced pluripotent stem cell (iPS cell) (Takahashi K et al, Cell. 2007 Nov. 30; 131(5): 861-72, which is incorporated herein by reference in its entirety), spermatogonial stem cell (Kanatsu-Shinohara M et al., Biol Reprod. 2007 January; 76(1): 55-62, which is incorporated herein by reference in its entirety), embryonic germ cell (Matsui Y et al, Cell. 1992 Sep. 4; 70(5): 841-7, which is incorporated herein by reference in its entirety), ES cell derived from cloned embryo obtained by nuclear transplantation (Wakayama T et al, Science. 2001 Apr. 27; 292(5517): 740-3, which is incorporated herein by reference in its entirety) and the like.

Neural stem cells and/or neural progenitor cells derived from pluripotent stem cells can be obtained by a method known per se. Examples of a method of producing neural stem cell and/or neural progenitor cell derived from pluripotent stem cell include a method of forming neural stem cells and/or neural progenitor cells by culturing pluripotent stem cells in suspension and performing embryoid body formation (Bain G et al, Dev Biol. 1995 April; 168(2): 342-57, which is incorporated herein by reference in its entirety, and the like), a method including culturing pluripotent stem cells by using stromal cells and the like as feeder cells, a method including culturing pluripotent stem cells in suspension in a serum-free medium containing bFGF (Watanabe K et al, Nat Neurosci. 2005 March; 8(3): 288-96, which is incorporated herein by reference in its entirety, and the like), a method including adhesion culture of pluripotent stem cells (ES cells etc.) in the presence of SMAD signal inhibitor Noggin and SB431542 (Chambers S M et al., Nat Biotechnol. 2009 March; 27(3): 275-80, which is incorporated herein by reference in its entirety), a method including culturing monolayer-cultured pluripotent stem cells (ES cells etc.) in the presence of glycogen synthase kinase 3 (GSK3) inhibitor, transforming growth factor β (TGF-β) inhibitor, Notch signal inhibitor (Li W et al, Proc Natl Acad Sci USA. 2011 May 17; 108(20): 8299-304, which is incorporated herein by reference in its entirety), and the like.

Preferably, the neural stem cells and/or neural progenitor cells to be used in the present invention are derived from ES cells or induced pluripotent stem cells, more preferably induced pluripotent stem cells.

Whether the cell is a neural stem cell can be continued by, for example, culturing the cells in suspension in a serum-free medium containing EGF and bFGF and, after a dispersion treatment of the cultured cell aggregate, subjecting the cell aggregate to adhesion culture to induce differentiation into nerve cell and glial cell.

In addition, neural stem cell can also be confirmed by a gene known to express in a neural stem cell, a transcription product thereof, a protein (neural stem cell marker) and the like.

As the neural stem cell marker, cytoskeletal protein Nestin (Science, 276, 66 (1997)), SOX1 (SRY (sex determining region Y)-box1), SOX2 (SRY (sex determining region Y)-box2), Pax6 (paired box 6), Ki67, Proliferating cell nuclear antigen (PCNA), fatty acid binding protein 7 (Fabp7, also called BLBP) and the like are known, and those of ordinary skill in the art can confirm the desired neural stem cell by appropriately combining these markers. Examples of the neural stem cells suitable for the present invention include, but are not limited to, SOX2-positive and Nestine-positive cells.

That a cell is a neural progenitor cell can be confirmed by, for example, culturing the cell, and inducing the cell to differentiate into a nerve cell.

As a gene expressed in neural progenitor cells, Tbr2 (T-box brain protein 2), MASH1 (Mammalian achaete-scute homolog 1), Nestine and the like can be mentioned. Examples of a neural progenitor cell suitable for the present invention include, but are not limited to, SOX2-negative and Nestine-positive cells.

Examples of a marker of the differentiated nerve cell include βIII tubulin, MAP2 (microtubule-associated protein) and the like.

In the present specification, maintenance of undifferentiation of neural stem cells and/or neural progenitor cells means that one or more of the cells formed by neural stem cells and/or neural progenitor cells after division continue to maintain properties of neural stem cells and/or neural progenitor cells, differentiation of neural stem cells and/or neural progenitor cells is suppressed, or neural stem cells and/or neural progenitor cells do not divide but continue to maintain properties of neural stem cells and/or neural progenitor cells. Whether the cells formed by neural stem cells and/or neural progenitor cells after division maintain properties of neural stem cells and/or neural progenitor cells can be confirmed by, for example, the aforementioned markers. In the present specification, that differentiation of neural stem cells and/or neural progenitor cells is suppressed means that the proportion of the differentiated cells (e.g., nerve cells) in the whole cells produced by neural stem cells and/or neural progenitor cells decreases. Suppression of differentiation may be suppression of differentiation of neural stem cells and/or neural progenitor cells into nerve cells and the like. Suppression of differentiation can be confirmed by, for example, the aforementioned differentiation markers (e.g., nerve cell markers such as βIII tubulin and the like).

In one embodiment, the neural stem cells and/or neural progenitor cells to be used in the present invention are isolated. The "isolation" means that an operation to remove factors other than the object components and cells has been performed and thus they are no longer in a naturally occurring state. The purity of the "isolated neural stem cells and/or neural progenitor cells" (percentage of the number of neural stem cells and/or neural progenitor cells in the total number of cells) is generally not less than 70%, preferably not less than 80%, more preferably not less than 90%, more preferably not less than 99%, most preferably 100%.

(3) Medium of the Present Invention

In one embodiment of the present invention, the present invention provides a medium for culturing neural stem cells and/or neural progenitor cells. The medium of the present invention provides effects of maintenance of undifferentiated state and multipotency of neural stem cells and/or neural progenitor cells, and promotion of proliferation thereof. In another embodiment, the medium of the present invention has an action to improve efficiency of induction of pluripotent stem cells into neural stem cells and/or neural progenitor cells. Since the medium of the present invention maintains undifferentiated state and multipotency of neural stem cells and/or neural progenitor cells and promotes proliferation thereof, a small number of induced neural stem cells and/or neural progenitor cells can be effectively proliferated, as a result of which efficiency of induction of neural stem cells and/or neural progenitor cells can be improved. In one embodiment of the present invention, the medium of the present invention is for maintaining undifferentiation of neural stem cells and/or neural progenitor cells, and for promoting proliferation of neural stem cells and/or neural progenitor cells. In another embodiment, the medium of the present invention is for induction of neural stem cells and/or neural progenitor cells, and for induction of neural stem cells and/or neural progenitor cells from pluripotent stem cells.

The medium of the present invention contains chelated iron. The chelated iron to be added is as mentioned above. The components other than chelated iron to be contained in the medium of the present invention are not particularly limited as long as the desired effects such as promotion of proliferation and maintenance of undifferentiated state of neural stem cells and/or neural progenitor cells and the like can be achieved, and a composition generally used for culturing neural stem cells and/or neural progenitor cells can be appropriately adopted.

The medium of the present invention provides an effect of promoting proliferation of neural stem cells and/or neural progenitor cells having undifferentiated state and multipotency. For example, the medium of the present invention provides an effect of promoting proliferation of neural stem cells and/or neural progenitor cells which are SOX2-positive Nestine-positive and/or SOX2-negative Nestine-positive.

In the present specification, that "the medium of the present invention promotes proliferation of neural stem cells and/or neural progenitor cells" means that, when neural stem cells and/or neural progenitor cells are cultured for a certain period (preferably not less than 4 days (e.g., 4 days)) in the medium, the number of the neural stem cells and/or neural progenitor cells is higher than when cultured in a control medium having the same composition except that chelated iron is not contained.

The medium of the present invention may be prepared using the medium generally used for culturing animal cells as a basal medium. The basal medium is not particularly limited as long as the desired effects such as promotion of proliferation and maintenance of undifferentiated state of neural stem cells and/or neural progenitor cells and the like can be achieved. For example, media generally used for culturing animal cells such as BME medium, BGJb medium, CMRL 1066 medium, Glasgow MEM medium, Improved MEM Zinc Option medium, IMDM medium, Medium 199 medium, Eagle MEM medium, αMEM medium, DMEM medium, F-12 medium, DMEM/F12 medium, IMDM/F12 medium, ham medium, RPMI 1640 medium, Fischer's medium, or mixed medium of these and the like can be mentioned. The medium of the present invention may be prepared using the medium generally used for culturing stem cells as a basal medium. As a commercially available basal medium for culturing stem cells, RHB medium (StemCells, Inc.), hESF-GRO medium (NIPRO CORPORATION), HESF-DIF medium (NIPRO CORPORATION), CSTI-7 (Cell Science & Technology Institute, Inc.) and the like can be mentioned.

To avoid contamination with chemically-undefined components, the medium to be used in the present invention is preferably a medium containing chemically-defined components (Chemically defined medium; CDM).

Since serum contains components that promote differentiation of neural stem cells and/or neural progenitor cells, the medium of the present invention is preferably a serum-free medium. The "serum-free medium" in the present invention means a medium free of unconditioned or unpurified serum. In the present invention, media containing purified components derived from blood or animal tissues (e.g., growth factors such as EGF, bFGF and the like) are also included in the serum-free medium as long as unconditioned or unpurified serum is not contained.

The serum-free medium may contain a serum replacement. Examples of the serum replacement include those appropriately containing serum albumin, fatty acid, collagen precursor, trace element, 2-mercaptoethanol, 3'thiolglycerol, equivalents of these and the like. Such serum replacement can be prepared by the method described in, for example, WO 98/30679, which is incorporated herein by reference in its entirety. As the serum replacement, a commercially available product may also be utilized. Examples of such commercially available serum replacement include, but are not limited to, Knockout™ Serum Replacement (manufactured by Life Technologies: hereinafter sometimes to be also indicated as KSR), Chemically-defined Lipid concentrate (manufactured by Life Technologies), Glutamax™ (manufactured by Life Technologies), and B27 (Life Technologies Inc.).

The medium of the present invention may further contain a medium additive. Examples of the medium additive include, but are not limited to, vitamins, non-essential amino acids such asglutamine and the like, proteins such as cytokines, growth factors and the like, L-ascorbic acid, phosphoric acid L-ascorbyl magnesium, pyruvic acid sodium, 2-aminoethanol, glucose, sodium hydrogen carbonate, HEPES, insulin, progesterone, sodium selenate, putrescine and the like. Additives are preferably contained in a known concentration range.

The medium of the present invention contains essential amino acids (L-lysine, L-leucine, L-isoleucine, L-threonine, L-valine, L-phenylalanine, L-histidine, L-tryptophan). The medium of the present invention preferably contains L-serine, L-cystine, glycine, L-cysteine, L-proline, L-methionine, L-glutamic acid, L-aspartic acid and L-alanine, L-glutamine, L-arginine, L-tyrosine, L-asparagine.

The medium of the present invention contains one or more, preferably two or more, more preferably not less than 3, further preferably not less than 4, medium additives selected from the group consisting of inositol, choline chloride, folic acid, D-calcium pantothenate, thiamine (vitamin B1), pyridoxine (vitamin B6), niacinamide, vitamin B12, riboflavin (vitamin B2), D-biotin, D-glucose, pyruvic acid sodium, hypoxanthine, thymidine, lipoic acid, and putrescine hydrochloride.

When the medium of the present invention is used for culturing neural stem cells and/or neural progenitor cells, the medium of the present invention preferably contains epithelial cell growth factor (EGF) and/or basic fibroblast growth factor (bFGF), more preferably bFGF.

In the present invention, while the upper limit of the amount of bFGF in the medium is not limited as long as the desired effects can be achieved, it is preferably not more than 1000 ng/ml, more preferably not more than 500 ng/ml, further preferably not more than 200 ng/ml.

In the present invention, while the lower limit of the amount of bFGF in the medium is not limited as long as the desired effects can be achieved, it is preferably not less than 0.1 ng/ml, more preferably not less than 1 ng/ml, further preferably not less than 10 ng/ml.

In the present invention, while the amount of bFGF in the medium is not limited as long as the desired effects can be achieved, it is preferably 0.1 ng/ml to 1000 ng/ml, more preferably 1 ng/ml to 500 ng/ml, further preferably 10 ng/ml to 200 ng/ml.

In one embodiment, the medium of the present invention contains bFGF (final concentration 10 ng/ml to 200 ng/ml). In addition, the medium of the present invention is preferable substantially free of a substance having an effect of promoting differentiation of neural stem cells and/or neural progenitor cells (to be also referred to as neuronal differentiation promoting substance in the present specification).

Examples of the neuronal differentiation promoting substance include BDNF (Brain-derived neurotrophic factor), GDNF (Glial cell line-derived neurotrophic factor), cAMP (Cyclic adenosine monophosphate), dbcAMP (dibutyryl cAMP), DAPT (tert-butyl (2S)-2-[[(2S)-2-[[2-(3,5-difluorophenyl)acetyl]amino]propanoyl]amino]-2-phenylacetate), compound E (N-[(1S)-2-[[(3S)-2,3-Dihydro-1-methyl-2-oxo-5-phenyl-1H-1,4-benzodiazepin-3-yl]amino]-1-methyl-2-oxoethyl]-3,5-difluorobenzeneacetamide), SU5402 (2-[(1,2-Dihydro-2-oxo-3H-indol-3-ylidene)methyl]-4-methyl-1H-pyrrole-3-propanoic acid), SU6668 (3-[2,4-dimethyl-5-[(E)-(2-oxo-1H-indol-3-ylidene)methyl]-1H-pyrrol-3-yl]propanoic acid; Orantinib; and 3-[2,4-dimethyl-5-[(E)-(2-oxo-1H-indol-3-ylidene)methyl]-1H-pyrrol-3-yl] propanoic acid).

Being substantially free of a neuronal differentiation promoting substance means that even when a neuronal differentiation promoting substance is contained, its amount cannot promote differentiation of neural stem cells and/or neural progenitor cells, and the amount is appropriately determined according to the kind of the neuronal differentiation promoting substance to be used. More preferably, the concentration of the neuronal differentiation promoting substance contained in the medium of the present invention is 0 μM.

When the medium of the present invention is used for induction of neural stem cells and/or neural progenitor cells, the medium of the present invention preferably contains a substance that promotes induction of neural stem cells and/or neural progenitor cells. A substance that promotes induction of neural stem cells and/or neural progenitor cells is appropriately selected according to the induction method of the neural stem cells and/or neural progenitor cells. Examples of the induction method of the neural stem cells and/or neural progenitor cells include the aforementioned induction method of neural stem cells and/or neural progenitor cells derived from pluripotent stem cells, method of directly inducing differentiation from fibroblasts and the like (Stem Cells. 2012 June; 30(6): 1109-19, which is incorporated herein by reference in its entirety) and the like.

The medium of the present invention may contain a fatty acid. Examples of the fatty acid to be contained in the medium of the present invention include, but are not limited to, oleic acid, linoleic acid, α-linolenic acid, γ-linolenic acid, palmitic acid, stearic acid, arachidonic acid, icosapentaenoic acid, docosahexaenoic acid, butyric acid, acetic acid, pulmitoleic acid, valeric acid (valerianic acid), caproic acid, enanthic acid (hepthylic acid), caprylic acid, pelargric acid, capric acid, lauric acid, myristic acid, pentadecylic acid, margaric acid, Khusenic acid, eleostearic acid, arachidic acid, 8,11-eicosadienoic acid, 5,8,11-eicosatrienoic, behenic acid, lignoceric acid, nervonic acid, cerotic acid, montanic acid, melissic acid and the like. The fatty acid to be contained in the medium of the present invention may be saturated fatty acid or unsaturated fatty acid.

The medium of the present invention can be used for any culture method such as adhesion culture, suspension culture, embedded culture, tissue culture and the like.

The medium of the present invention can be preferably used for culturing neural stem cells and/or neural progenitor cells derived from any animals. The neural stem cells and/or neural progenitor cells that can be cultured using the medium of the present invention include neural stem cells and/or neural progenitor cells derived from, for example, rodents such as mouse, rat, hamster, guinea pig and the like, lagomorpha such as rabbit and the like, ungulata such as swine, bovine, goat, horse, sheep and the like, carnivora such as canine, feline and the like, primates such as human, monkey, cynomolgus monkey, marmoset, orangutan, chimpanzee and the like, and the like, preferably, neural stem cells and/or neural progenitor cells derived from human.

The medium of the present invention preferably contains insulin, $NaHCO_3$, selenium, ethanolamine, bFGF as well as chelated iron. More preferably, the medium of the present invention is prepared with DMEM/F-12 medium as a basal medium, and contains insulin, $NaHCO_3$, selenium, ethanolamine, bFGF, as well as chelated iron.

In one embodiment the medium of the present invention is prepared with DMEM/F-12 medium as a basal medium, and contains albumin (0.5 mg to 5 mg/ml), insulin (5 µg/ml to 1 mg/ml), $NaHCO_3$ (100 µg/ml to 5 mg/ml), sodium selenate (2 ng/ml to 1 µg/ml), ethanolamine (100 ng/ml to 100 µg/ml), and bFGF (10 ng/ml to 200 ng/ml), as well as chelated iron.

In one embodiment, the medium of the present invention is a medium containing holotransferrin (0.5 to 6.5 µg/ml) and bFGF (10 ng/ml to 200 ng/ml), wherein the amount of iron of a high molecular form in the medium is 3 ppb to 7 ppb. Preferably, the medium of the present invention contains holotransferrin (0.5 to 6.5 µg/ml) having an iron content of 200 µg/g to 500 µg/g and bFGF (10 ng/ml to 200 ng/ml). Further preferably, the medium of the present invention contains holotransferrin (0.5 to 6.5 µg/ml) having an iron content of 380 µg/g and bFGF (10 ng/ml to 200 ng/ml).

(4) Method of the Present Invention

In one embodiment of the present invention, the present invention provides a method of culturing neural stem cells and/or neural progenitor cells, which comprises adding chelated iron to a medium. The method is also a method of proliferating neural stem cells and/or neural progenitor cells and maintaining undifferentiation thereof. In another embodiment, a method of improving efficiency of induction of neural stem cells and/or neural progenitor cells from pluripotent stem cells and the like is provided. Since the method of the present invention maintains undifferentiated state and multipotency of neural stem cells and/or neural progenitor cells and promotes proliferation thereof, and a small number of induced neural stem cells and/or neural progenitor cells can be effectively proliferated, as a result of which efficiency of induction of neural stem cells and/or neural progenitor cells can be improved.

In one embodiment of the present invention, the method of the present invention includes a step of culturing neural stem cells and/or neural progenitor cells in the medium of the present invention. In one embodiment of the present invention, the method of the present invention includes a step of culturing cells capable of inducing neural stem cells and/or neural progenitor cells in the medium of the present invention. In another embodiment of the present invention, the method of the present invention includes a step of adding chelated iron to a medium free of chelated iron and culturing in the presence of the chelated iron for a certain period.

The neural stem cells and/or neural progenitor cells to be used for the method of the present invention are preferably neural stem cells and/or neural progenitor cells which are SOX2-positive Nestine-positive and/or SOX2-negative Nestine-positive.

While the period of culturing neural stem cells and/or neural progenitor cells in the culture method of the present invention is not particularly limited as long as the desired effects such as promotion of proliferation and maintenance of undifferentiated state of neural stem cells and/or neural progenitor cells and the like can be achieved, it is generally not less than 2 days, preferably not less than 4 days, further preferably not less than 8 days.

When neural stem cells and/or neural progenitor cells are cultured for not less than 4 consecutive days, the medium is preferably exchanged once in 3 days, preferably once in 2 days.

The neural stem cells and/or neural progenitor cells cultured in the medium of the present invention are harvested, a part or entirety thereof is passaged in a fresh medium of the present invention, and continuously cultured, whereby the neural stem cells and/or neural progenitor cells can be passaged while maintaining the undifferentiated state of the neural progenitor cells and promoting proliferation thereof.

While the time of addition of the chelated iron to the medium in the method of the present invention is not particularly limited as long as it is such length of time that can achieve the desired effects such as promotion of proliferation and maintenance of undifferentiated state of neural stem cells and/or neural progenitor cells and the like, it is preferable to perform culturing in a medium containing chelated iron throughout the entire culture period. The composition of the medium is as described above.

When the efficiency of induction of neural stem cells and/or neural progenitor cells is improved in the method of the present invention, the neural stem cells and/or neural progenitor cells are induced according to a known induction method of neural stem cells and/or neural progenitor cells except that the medium to be used contains chelated iron (e.g., the aforementioned induction method of neural stem cells and/or neural progenitor cells derived from pluripotent stem cells, method of directly inducing differentiation from fibroblasts and the like, though not limited to these).

When neural stem cells and/or neural progenitor cells are cultured in the method of the present invention, they can be cultured according to a known method such as adhesion culture, suspension culture, tissue culture and the like except that the medium to be used contains chelated iron. The culture method can be appropriately selected according to the object. Examples of the adhesion culture method of neural stem cells and/or neural progenitor cells include the methods described in Flanagan L A et al, J Neurosci Res. 2006 April; 83(5): 845-56, Conti L et al, PLoS Biology., 2005 September; 3(9): e283, which are incorporated herein by reference in their entireties, and the like. Suspension culture of neural stem cells and/or neural progenitor cells refers to culturing neural stem cells and/or neural progenitor cells under the condition under which they are non-adhesive to an incubator or feeder cells (when used) in the medium.

Examples of the suspension culture method of neural stem cells and/or neural progenitor cells include neurosphere method (Reynolds B A and Weiss S., Science, USA, 1992 Mar. 27; 255(5052): 1707-10, which is incorporated herein by reference in its entirety), Serum-free Floating culture of Embryoid Bodies-like aggregates method (SFEB method, SFEBq method; Watanabe et al, Nature Neuroscience 8, 288-296 (2005), which is incorporated herein by reference in its entirety) and the like. Tissue culture of neural stem cells and/or neural progenitor cells is a method of culturing a tissue containing neural stem cells and/or neural progenitor cells as a tissue section such as slice and the like or the whole tissue. Examples of the tissue culture of neural stem cells and/or neural progenitor cells include slice culture methods described in O'Rourke N A et al, Science. 1992 Oct. 9; 258(5080): 299-302, Komuro H et al, Science. 1992 Aug. 7; 257(5071): 806-9, which are incorporated herein by reference in their entireties, and the like.

In the present invention, the presence or absence and the level of proliferation of neural stem cells and/or neural progenitor cells can be evaluated by measuring the number of viable cells by using a cell staining reagent such as Trypan Blue and the like. When neurosphere is foamed by suspension culture, they can be evaluated by measuring the size of the neurosphere to be formed, or the number of cells constituting the neurosphere.

In the method of the present invention, an incubator to be used for culturing neural stem cells and/or neural progenitor cells is not particularly limited as long as the neural stem cells and/or neural progenitor cells can be cultured. Examples thereof include flask, tissue culture flask, dish, petri dish, tissue culture dish, multidish, microplate, microwell plate, multiplate, multiwell plate, microslide, chamber slide, schale, tube, tray, culture bag, and roller bottle.

An incubator used for culturing neural stem cells and/or neural progenitor cells may be cell adhesive or cell non-adhesive, and is appropriately selected according to the object. When neural stem cells and/or neural progenitor cells are cultured by suspension culture, the incubator is preferably cell non-adhesive.

When neural stem cells and/or neural progenitor cells are cultured by adhesion culture, the incubator is preferably cell adhesive. A cell adhesive incubator may be coated with any cell supporting substrate such as extracellular matrix (ECM) and the like or an artificial material mimicing the function thereof, for the purpose of improving the adhesiveness of the cells to the surface of the incubator. The cell supporting substrate may be any substance aiming at adhesion of stem cells or feeder cells (when used).

Other culture conditions can be appropriately determined. For example, the culture temperature is not particularly limited as long as the desired effects such as promotion of proliferation and maintenance of undifferentiated state of neural stem cells and/or neural progenitor cells and the like can be achieved. It is about 30 to 40° C., preferably about 37° C. The $CO_2$ concentration is about 1 to 10%, preferably about 2 to 5%. The oxygen concentration is generally 1 to 40%, and is appropriately selected according to culture conditions and the like.

(5) Culture Composition Comprising Medium Containing Chelated Iron and Neural Stem Cells and/or Neural Progenitor Cells The present invention further provides a culture composition comprising the above-mentioned medium of the present invention and neural stem cells and/or neural progenitor cells (also referred to as the culture composition of the present invention in the present specification). The culture composition includes a resultant product obtained by culturing the cells. The definition and embodiment of each term relating to the culture composition of the present invention are the same as those described above.

The neural stem cells and/or neural progenitor cells in the culture composition of the present invention are cells that are viable and proliferative.

The purity of the neural stem cells and/or neural progenitor cells in the culture composition of the present invention (percentage of the number of neural stem cells and/or neural progenitor cells in the total number of cells) is generally not less than 70%, preferably not less than 80%, more preferably not less than 90%, further preferably not less than 99%, most preferably 100%.

In the culture composition of the present invention, neural stem cells and/or neural progenitor cells are present in the medium of the present invention. In one embodiment, the culture composition of the present invention is a suspension of neural stem cells and/or neural progenitor cells in the medium of the present invention. The culture composition of the present invention may be sealed in an appropriate container.

In one embodiment, the culture composition of the present invention can be provided in a cryopreserved state. The culture composition of the present invention can be cryopreserved, and can be used by thawing and raising from sleep as necessary. For cryopreservation, a known cell cryopreservation method can be used. As an example of cryopreservation, dimethyl sulfoxide is added to the culture composition of the present invention, and the culture composition of the present invention is preserved at −80 to −200° C., preferably −196° C. (in liquid nitrogen).

Other features of the invention will become apparent in the course of the following descriptions of exemplary embodiments which are given for illustration of the invention and are not intended to be limiting thereof.

EXAMPLES

Example 1

Functional Evaluation of Holotransferrin (1) Long-Term Self-Renewing Neuro Epithelial-Like Stem Cells (Hereinafter LtNES Cells) Induction Method EB was formed from iPS cells, and for 4 days, cultured in a medium obtained by adding holotransferrin (final concentration 0.5 to 10 μg/ml), ethanolamine (final concentration 5 to 50 μM), and bFGF (final concentration 5 to 100 ng/ml) to a medium corresponding to a composition of E6 medium (Life Technologies or STEMCELL Technologies) without ascorbic acid and transferrin for 4 days. EB was seeded in a dish coated with poly-L-ornithine (PO), cultured for about 10 days in the above-mentioned medium, and formation of a rosette-like structure was confirmed. The rosette part was removed, and subjected as neurosphere to suspension culture in the above-mentioned medium for about 7 days. The neurosphere was dispersed in trypsin/EDTA, and cultured in RHB-A medium on a dish coated with PO/laminin to give LtNES cells. The LtNES cells are composed of a mixture of neural stem cells and neural progenitor cells.

The above-mentioned E6 medium (Essential 6 medium) is produced by an E8 medium-based production method and does not contain bFGF and TGFβ as described in the homepage of Life Technologies <URL:http://www.lifetechnologies.com/order/catalog/product/A1516401>. E8 medium (Essential 8 medium) is described in Nat Methods 2011 May; 8(5):424-429, which is incorporated herein by reference in its entirety).

The components of the above-mentioned E6 medium are also described in the summary of Stem Cells. 2014 April; 32(4), 1032-42, which is incorporated herein by reference in its entirety.

(2) Culture Method of LtNES Cells

LtNES cells induced from human pluripotent stem cells were cultured in RHB-A medium, 20 ng/ml bFGF under 37° C., 5% $CO_2$ environment. For passage of LtNES cells, they were incubated in TrypLE Select at 37° C. for 1 min, diluted with the medium and converted to single cells by pipetting. The dispersed cells were seeded in the above-mentioned medium at $1.5 \times 10^5$ cells/well (6-well plate) and cultured under 37° C., 5% $CO_2$ environment. Dead cells were stained with Trypan Blue (Life Technologies Inc.) and the cell number was measured by hemocytometer.

(3) Functional Evaluation of Holotransferrin

Albumin (final concentration 0.5 to 5 mg/ml), ethanolamine (final concentration 5 to 50 μM) and bFGF (final concentration 5 to 100 ng/ml) were added to a medium corresponding to a composition of E6 medium (Life Technologies or STEMCELL Technologies) without ascorbic acid and transferrin to produce a test basal medium.

Holotransferrin (Sigma Aldrich) was added to the test basal medium at a final concentration of 0, 1.0, 2.5, 5, 7.5 μg/ml to give test media.

Using each test medium, LtNES cells induced from human pluripotent stem cells were cultured. The cells were cultured in an incubator at 37° C., 5% $CO_2$ atmosphere. The medium was exchanged every two days, and the cells were cultured for 4 to 5 days. After culturing, cell dispersion treatment was performed by adding TrypLE Select instead of the test medium and then incubating it at 37° C. for 1 min. TrypLE Select was diluted with the medium, pipetting was performed to give single cells, and the number of the cells was counted and evaluated. Dead cells were stained with Trypan Blue (Life Technologies Inc.) and the cell number was measured by hemocytometer.

Figure 1:
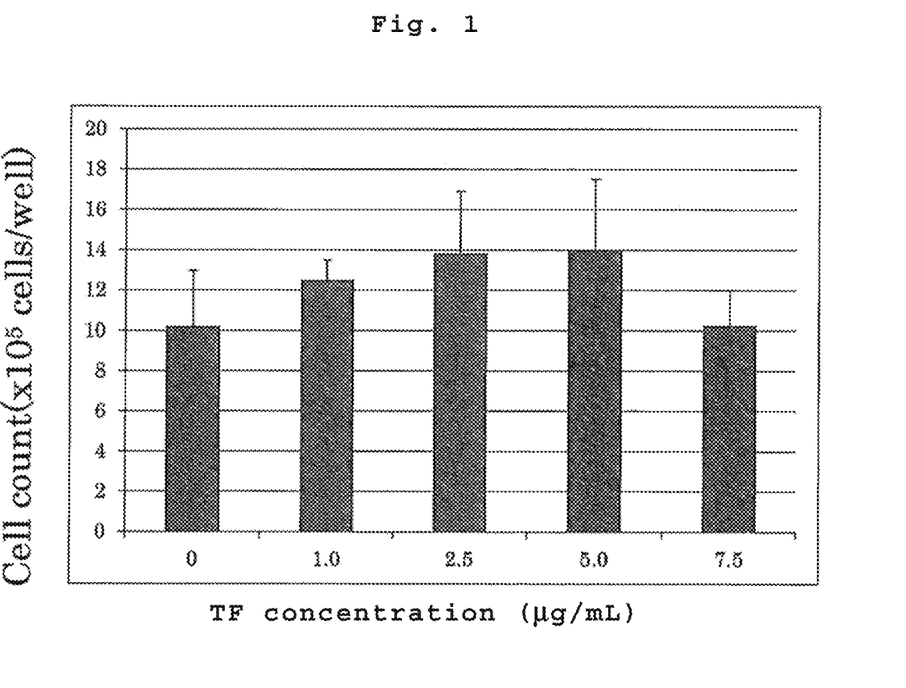
FIG. 1 shows the proliferation of neural stem cells and/or neural progenitor cells in a medium added with holotransferrin. The vertical axis shows cell number, and the horizontal axis shows the final concentration (µg/ml) of holotransferrin contained in the medium. The neural stem cells and/or neural progenitor cells showed good proliferation when the concentration of holotransferrin in the medium was 1.0 to 5.0 µg/ml.
Figure 2:
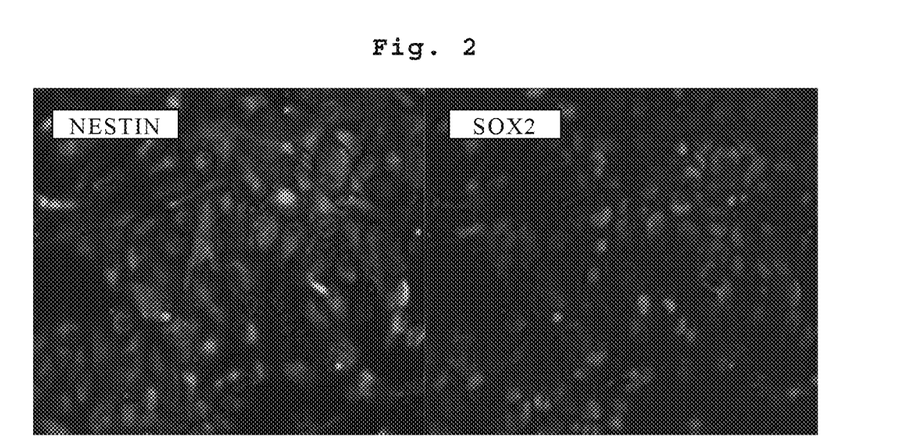
FIG. 2 shows the results of immunostaining of neural stem cells and/or neural progenitor cells cultured in a medium having a holotransferrin content of 2.5 μg/ml. Many Nestine (green)-positive and SOX2 (red)-positive neural stem cells, and Nestine-positive SOX2-negative neural progenitor cells were observed.

The results are shown in FIG. 1. The cell number increased most in 2.5 μg/ml holotransferrin-added medium and 5 μg/ml holotransferrin-added medium, and the cells showed good proliferation also in 1 μg/ml holotransferrin-added medium.

The iron content of holotransferrin used in this Example was measured to find that the content of iron of a high molecular form in a transferrin sample (1 mg/ml transferrin) was 380 ppb. The iron content (saturated) that can be bonded to 1 mg/ml of transferrin is 1400 ppb by calculation. Therefore, it was found that holotransferrin used in this example shows a ratio of iron bonded to transferrin of about 27%.

(4) Analysis of Total Amount of Iron in Medium

To examine whether the promotion of proliferation of neural stem cells and/or neural progenitor cells by the addition of holotransferrin (Tf) depends on an increase in the iron content, the iron content of each test medium was measured. In addition, the amounts of Mn, Ni, Co, Cu, Zn, Se other than iron were also measured.

Each test medium was diluted, introduced into Inductively coupled plasma-mass spectrometry apparatus (hereinafter ICP-MS, Thermo Fisher Scientific Inc.), and each element was detected and quantified by the External Calibration Method.

The results are shown in Table 1.

TABLE 1

Analysis results of total amount of iron in medium

| holotransferrin concentration (μg/ml) | Fe (m/z54) |
|---|---|
| 0 | 50 |
| 1 | 60 |
| 2.5 | 50 |
| 5 | 60 |
| 7.5 | 60 |

Regardless of the amount of holotransferrin added to the medium, the iron content of the medium was almost constant. Also, the metals other than iron showed an almost constant metal amount in the medium regardless of the amount of holotransferrin added to the medium.

(5) Analysis of Iron Content According to the Form of Iron

The iron content of the medium was measured according to the form of iron.

To analyze iron content of the medium according to the form of iron, SEC-ICP-MS (ICP-MS, Agilent Technologies, connected to size-exclusion chromatography (SEC, Thermo Fisher Scientific Inc.)) was performed. A medium was introduced into size-exclusion chromatography, and the eluent was analyzed by ICP-MS connected online. Each element was detected by ICP-MS, and quantified by External Calibration Method.

The results are shown in Table 2.

TABLE 2

Analysis results of iron content according to the form of iron

| | iron analysis by chemical form | |
|---|---|---|
| holotransferrin concentration (μg/ml) | iron of high molecular form (ppb) | iron of low molecular form (ppb) |
| 0 | 2 | 40 |
| 1 | 4 | 33 |
| 2.5 | 5 | 26 |
| 5 | 6 | 23 |
| 7.5 | 8 | 18 |

As a result, it was clarified that iron of a high molecular form increases according to the amount of holotransferrin added.

Example 2

Immunohistochemical Staining of Neural Stem Cells and Neural Progenitor Cells

It was demonstrated by immunohistochemical staining that the cells that showed good proliferation in holotransferrin-added medium were neural stem cells.

Figure 3:
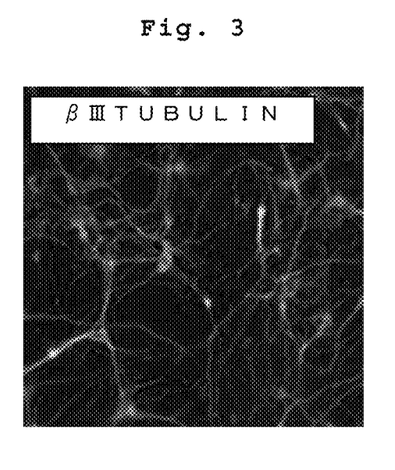
FIG. 3 shows the results of immunostaining of cells obtained by culturing neural stem cells and/or neural progenitor cells in a medium having a holotransferrin content of 2.5 μg/ml, and inducing differentiation thereof. Nerve cell marker βIII tubulin (green)-positive cells were observed in a culture dish after differentiation induction.

In the same manner as in Example 1, a medium added with holotransferrin to a final concentration of 2.5 μg/ml was produced, and cells were cultured under conditions similar to those in Example 1. After culturing, the cells were fixed and immunostained using antibody against Nestine as a neural stem/progenitor cell marker and antibody against SOX2 as a neural stem cell marker. The results are shown in FIG. 3.

Almost all of the cells on the culture dish were positive to Nestine as a marker of neural stem cell and neural progenitor cell. A large part of the cells was positive to SOX2 as a neural stem cell marker. Therefore, it was suggested that the cells that showed good proliferation in Example 2 were neural stem cells, which are Nestine-positive SOX2-positive.

Example 3

Induction of Nervous System Cells

To demonstrate that the cells cultured in the holotransferrin-added medium can actually differentiate, a differentiation induction experiment was performed.

In the same manner as in Example 1, a medium added with holotransferrin to a final concentration of 2.5 μg/ml was produced, and cells were cultured under conditions similar to those in Example 1. After culturing, cell dispersion treatment was performed by adding TrypLE Select instead of the test medium and then incubating it at 37° C. for 1 min. TrypLE Select was diluted with the medium, pipetting was performed, and the cells were seeded at $1.5 \times 10^5$ cells/well in a 48-well plate coated with Poly-L-ornithine/fibronectin. The cells were cultured in a Media hormone mix medium added with 1×B27 supplement for 20 days. The cells were cultured in an incubator at 37° C., 5% $CO_2$ atmosphere. The medium was exchanged every two days.

After culturing, the cells were fixed and immunostained by fluorescent antibody method using antibody against βIII tubulin as a nerve cell marker.

It was shown that the cells after differentiation induction contained differentiated nerve cells, which are βIII tubulin-positive.

INDUSTRIAL APPLICABILITY

According to the present invention, cell proliferation can be promoted while maintaining undifferentiated state and multipotency of neural stem cells and/or neural progenitor cells, and the personnel costs and economical costs necessary for culturing neural stem cells and/or neural progenitor cells can be reduced.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of proliferating neural stem cells and/or neural progenitor cells while maintaining an undifferentiated state, comprising culturing said neural stem cells and/or neural progenitor cells in a chemically-defined culture medium which comprises chelated iron, wherein said chelated iron is bound to transferrin and present in said medium in an amount of 3 to 7 ppb.

2. The method according to claim 1, wherein said neural stem cells and/or neural progenitor cells are obtained from pluripotent stem cells.

3. The method according to claim 1, wherein said transferrin is present in said chemically-defined culture medium in an amount of not less than 0.5 μg/ml and not more than 6.5 μg/ml.

4. The method according to claim 1, wherein said transferrin is present in said chemically-defined culture medium in an amount of not less than 0.1 μg/ml and not more than 1.8 μg/ml.

* * * * *